US009835576B2

(12) United States Patent
Polesel Maris et al.

(10) Patent No.: US 9,835,576 B2
(45) Date of Patent: Dec. 5, 2017

(54) BIOSENSOR AND METHOD OF MANUFACTURING SUCH A BIOSENSOR

(75) Inventors: Jérôme Polesel Maris, Gif sur Yvette (FR); Thomas Berthelot, Les Ulis (FR)

(73) Assignee: Commissariat A L'Energie Atomique Et Aux Energies Alternatives, Paris (FR)

( * ) Notice: Subject to any disclaimer, the term of this patent is extended or adjusted under 35 U.S.C. 154(b) by 0 days.

(21) Appl. No.: 14/000,957

(22) PCT Filed: Feb. 14, 2012

(86) PCT No.: PCT/IB2012/050664
§ 371 (c)(1),
(2), (4) Date: Aug. 22, 2013

(87) PCT Pub. No.: WO2012/114227
PCT Pub. Date: Aug. 30, 2012

(65) Prior Publication Data
US 2013/0327649 A1    Dec. 12, 2013

(30) Foreign Application Priority Data
Feb. 22, 2011 (FR) ...................................... 11 00521

(51) Int. Cl.
| | | |
|---|---|---|
| *G01N 5/00* | (2006.01) | |
| *H05K 1/03* | (2006.01) | |
| *H01K 3/00* | (2006.01) | |
| *G01N 27/327* | (2006.01) | |
| *G01N 29/02* | (2006.01) | |
| *G01N 29/036* | (2006.01) | |
| *B82Y 15/00* | (2011.01) | |
| *B82Y 40/00* | (2011.01) | |

(52) U.S. Cl.
CPC ......... *G01N 27/327* (2013.01); *G01N 29/022* (2013.01); *G01N 29/036* (2013.01); *B82Y 15/00* (2013.01); *B82Y 40/00* (2013.01); *G01N 2291/0255* (2013.01); *G01N 2291/0257* (2013.01); *G01N 2291/0427* (2013.01)

(58) Field of Classification Search
CPC ... G01N 2291/0255; G01N 2291/0257; G01N 2291/0427; G01N 29/022; G01N 29/036; G01N 27/327; B82Y 15/00; B82Y 40/00
See application file for complete search history.

(56) References Cited

U.S. PATENT DOCUMENTS

| | | | | |
|---|---|---|---|---|
| 2,459,089 | A | | 1/1949 | Orr |
| 6,099,132 | A | * | 8/2000 | Kaeriyama ........ G02B 26/0841 359/225.1 |
| 6,866,819 | B1 | * | 3/2005 | Chandra ................ G01N 27/12 422/50 |
| 2004/0208788 | A1 | * | 10/2004 | Colton .................... G01Q 70/18 422/68.1 |
| 2007/0169553 | A1 | * | 7/2007 | Mutharasan ............. G01H 11/08 73/579 |
| 2009/0117391 | A1 | | 5/2009 | Mevellec et al. |
| 2010/0268479 | A1 | | 10/2010 | Potyrailo et al. |
| 2010/0310800 | A1 | | 12/2010 | Berthelot et al. |

FOREIGN PATENT DOCUMENTS

| | | |
|---|---|---|
| FR | 0 758 660 A | 1/1934 |
| FR | 0 857 260 A | 9/1940 |
| FR | 0 857 269 A | 9/1940 |
| FR | 0 952 891 A | 11/1949 |
| FR | 0 955 859 A | 1/1950 |
| FR | 2 910 006 A1 | 6/2008 |
| FR | 2 910 011 A1 | 6/2008 |
| WO | WO-2005/121769 A1 | 12/2005 |

OTHER PUBLICATIONS

Häfliger, Daniel, et al. "Dry release of all-polymer structures." Microelectronic Engineering 78 (2005): 88-92.*
Marie, Rodolphe, et al. "Adsorption kinetics and mechanical properties of thiol-modified DNA-oligos on gold investigated by microcantilever sensors." Ultramicroscopy 91.1 (2002): 29-36.*
Wang, Yuli, et al. "Surface graft polymerization of SU-8 for bio-MEMS applications." Journal of Micromechanics and Microengineering 17.7 (2007): 1371.*
International Search Report and Written Opinion for Application No. PCT/IB2012/050664, dated May 3, 2012.
Edqvist, E. et al., *Gentle Dry Etching of P(VDF-TrFE) Multilayer Micro Actuator Structures by Use of an Inductive Coupled Plasma*, Journal of Micromechanics & Microengineering, vol. 18, No. 1 (2008).
Egitto, F.D., *Plasma Etching and Modification of Organic Polymers*, Pure Appl. Chem., and Ninth International Symposium on Plasma Chemistry, vol. 62, No. 9 (1989) oages 1699-1708.
Egitto, F.D. et al., *Modification of Polytetrafluoroethylene and polyethylene surfaces downstream from Helium Microwave Plasmas*, Polymer Degradation and Stability, vol. 30, No. 3 (1990) pp. 293-308.
Formanek, F. et al., *Selective Electroless Plating to Fabricate Complex Three-dimenstional Metallic Micro/Nanostructures*, Applied Physics Letters, vol. 88, No. 8 (2006).
Kaneko, K. et al., *Two-Photon Photoreduction of Metallic Nanoparticle Gratings in a Polymer Matrix*, Applied Physics Letters, vol. 83, No. 7 (2003) pp. 1426-1428.
Ozkaraoglu, E. et al., *Preparation of Au and Au—Pt Nanoparticles within PMMA matrix using UV and X-ray Irradiation*Polymer, vol. 50, No. 2 (2009) pp. 462-466.
Snis, N. et al., *Monolithic Fabrication of Multilayer P(VDF-TrFE) Cantilevers*, Sensors and Actuators A, vol. 144, No. 2 (2008) pp. 314-320.

* cited by examiner

*Primary Examiner* — Robert Eom
(74) *Attorney, Agent, or Firm* — Alston & Bird LLP

(57) ABSTRACT

A method of manufacturing a biosensor having a microbeam linked to a support, at least one electrode a biological molecule A grafted onto the microbeam in a different zone from the zone where the electrode is embedded, and a mechanoelectrical transducer for converting variations of the mechanical properties of the microbeam into an electrical signal, when the biological molecule A is placed in contact with a biological molecule B to be detected and/or quantified. The method includes: formation of an electrode on fluoropolymer material sheet, passivation of the electrode(s), creation of the form of the biosensor in the sheet of polymer material and separation of this form from the sheet, functionalization either of a prefunctionalized zone or of a zone of the microbeam, this zone being different from the zone wherein the electrode is embedded, and grafting of a biological molecule A onto the functionalized zone.

24 Claims, No Drawings

BIOSENSOR AND METHOD OF MANUFACTURING SUCH A BIOSENSOR

BACKGROUND

The invention relates to a process for the fabrication of a biosensor.

Most chemical sensors based on cantilevers or microbeams use the well-known silicon technology.

These chemical sensors are functionalized with molecules which can have a specific interaction with the biological material.

The term then used is biosensors.

The uses of these highly sensitive sensors relate to the field of proteomics, of DNA or RNA strand hybridization and of cell culturing and screening.

The detection of the specific interaction is linked to the changes in weight or of force applied to a cantilever, or microbeam, also known as microlever.

This mechanical change is detected by a sensor external or internal to the cantilever. The silicon-based cantilevers, or microbeams, can be placed in series in the form of a matrix of sensors for improving the measurement statistics and also the signal-to-noise ratio, but also so as to have various specific chemical interactions at the same time. However, the schemes for external detection of the deflection of the silicon microbeam use mainly optical detection by reflection of a laser beam, which is known to those skilled in the art. This method is not very suitable for detecting deflection of a matrix of cantilevers because of difficulties in setting up one or more lasers and/or a lens for the serial or parallel reading of a whole matrix of microbeams. This will be all the more true if the matrix contains a very large number (more than about ten) microlevers operating simultaneously. Furthermore, poorly controlled air/liquid interfaces can generate measurement artifacts which prevent stable detection of the deflection of the microbeam in a biological solution.

Therefore, in order to remove these technical impediments of bulk detection of a matrix of sensors, internal detection such as with a piezoresistive, piezoelectric or magneto-impedance sensor has been used inside the microbeam.

Each embedded sensor is addressed by metal electrodes.

The detection of the mechanical change, when the biomolecule functionalizing the biosensor is brought into contact with the biomolecule or the analyte to be detected and/or quantified, can be carried out a) in dynamic mode when the cantilever is set to resonate at a frequency close to its resonant frequency in order to increase the sensitivity of the detection, or b) in static mode by detection of the deflection of the microbeam due to the modification of the surface stress of the microbeam during the capturing of the biomolecules.

Silicon technology is very expensive for using such internal sensors integrated into cantilevers of a few micrometers or even millimeters with electrodes. Furthermore, the electrodes conveying the electrical signal resulting from the internal sensor of the microlever are in direct contact with the biological solution in which the microlever operates. Given the highly conductive and ionic nature of the biological solution, and for obvious reasons of problems of short-circuiting and/or of corrosion of the metal of which the electrodes are composed, this device may not work in this case.

SUMMARY

The invention aims to remove the impediment of bulk detection of a matrix of microlevers with an integrated sensor operating in a biological solution by proposing a novel process for the fabrication of biosensors based on fluoropolymer materials, in particular piezoelectric materials, for fabricating biosensors which are equivalent to silicon-technology-based biosensors but are less expensive in comparison therewith.

In the description which follows, the following terms have the following meaning:

"VUV radiation": (Vacuum UltraViolet) radiation with a wavelength of 200 to 100 nm, in the UV-C category, "UV radiation": radiation emitting at a wavelength of 400 to 280 nm, in the UV-A and UV-B category, "positive or positive-type photosensitive resin": photosensitive resin for which the part exposed to UV or VUV radiation becomes soluble in a revealing agent and/or the portion of photosensitive resin not exposed remains insoluble, "negative or negative-type photosensitive resin": photosensitive resin for which the part exposed to UV or VUV radiation becomes insoluble in a revealing agent and/or the portion of photosensitive resin not exposed remains soluble.

Examples of positive photosensitive resins usable in the invention are the Positiv 20® resins (Kontakt Chemie) or AZ 9260®, S1818® and SJR 5740® resins from the company MicroChem Corp. (Newton, USA).

In order to eliminate the irradiated resin zones, use may be made of the following revealing agents: a $KOH.H_2O$ or $NaOH.H_2O$ solution at 0.25 mol/l. For total elimination of the resin (irradiated or nonirradiated), use will be made of a solvent of acetone or DMSO (dimethyl sulfoxide) type.

The negative or negative-type photosensitive resins usable in the invention are the following resins: AZ resin series from MicroChemicals GmbH (Ulm, Germany) such as the AZ5214E® resin, or SU8-2000® or SU8-3000® from MicroChem Corp. (Newton, USA).

In order to eliminate the nonirradiated resin zones, use may be made of the following revealing agents: PGMEA (propylene glycol monomethyl ether acetate) for the SU8® resin, or the revealing agent AZ 351B® or AZ 726® for the AZ5214E® resin. For total elimination of the resin (irradiated or nonirradiated), use will be made of a solvent of the Negative resist remover 1651761® type (Sigma-Aldrich).

"mechanical property of the microbeam": change in weight, in resonant frequency, in quality factor, in surface mechanical stress or in stiffness constant of the microbeam.

DETAILED DESCRIPTION

The biosensors of the invention comprise, expressed in their simplest form:
- a microbeam, also called cantilever, which is the mobile part of the biosensor, connected to a support,
- at least one electrode, at least one part of which is embedded in the microbeam,
- at least one biological molecule A grafted onto the microbeam in a zone different than the zone wherein the electrode(s) is (are) embedded,
- a mechanoelectrical transducer for converting variations in the mechanical properties of the microbeam into an electrical signal, when the biological molecule A is brought into contact with a biological molecule B to be detected and/or quantified.

The mechanoelectrical transducer uses a different detection of the mechanical properties of the microbeam according to the type of biosensor used.

When the biosensor comprises only an electrode, a beam deflection generating a variation in the electrical resistance of the electrode formed on the cantilever is detected: the detection is said to be of piezoresistive type.

When the biosensor comprises just one electrode but also a pad made of a ferromagnetic material on the part of the electrode embedded in the microbeam, the variation in the impedance of the ferromagnetic material when the molecule A is brought into contact with the molecule B to be detected and/or quantified is measured.

The preferred ferromagnetic metals used in the invention to form the metal pad are chosen from ferromagnetic metals with a low coercive field, i.e. less than or equal to 2 Oersted.

The preferred metals are nickel, iron, cobalt or an alloy or mixture of at least two of them.

The detection is carried out by magnetoimpedance.

When the biosensor comprises two electrodes on the same face of the biosensor, a change in the resonant frequency of the microbeam via a change in weight when the biomolecule A is brought into contact with the molecule B to be detected and/or quantified is detected.

The detection is of piezoelectric type.

When the biosensor comprises two electrodes, one on one face of the biosensor and the other on the other face, the variation in the resonant frequency of the microbeam via a change in weight when the biomolecule A is brought into contact with the molecule B to be detected and/or quantified is measured.

The detection is of piezoelectric type.

When the biosensor comprises three electrodes, two electrodes on a first face of the biosensor and the other on the other face opposite the two electrodes of the first face, the change in resonant frequency when the molecule A is brought into contact with the molecule B to be detected and/or quantified is detected.

The detection is of the piezoelectric type.

The essential feature of the biosensor of the invention is that the microbeam connected to a support is made of a fluoropolymer material, which optionally has piezoelectric properties, these properties being essential when the type of detection is a piezoelectric detection.

The microbeam is integral with the support which therefore also consists of the same fluoropolymer material.

The preferred fluoropolymer materials used in the invention are, when the biosensor is not a piezoelectric-detection biosensor, polyvinylidene fluoride (PVDF), or a copolymer of polyvinylidene fluoride and of trifluoroethylene P(VDF-TrFe), or a tetrafluoroethylene polymer (PTFE). When the biosensor according to the invention is a piezoelectric-detection biosensor, it is necessary for the fluoropolymer material used to be a fluoropolymer material which has piezoelectric properties. The examples of such materials are PVDF and P(VDF-TrFe) having piezoelectric properties.

Thus, the process of the invention makes it possible to fabricate a biosensor comprising:
  a microbeam, which is the mobile part of the biosensor, connected to a support,
  at least one electrode, at least one part of which is embedded in the microbeam,
  at least one biological molecule A grafted onto the microbeam in a zone different than the zone wherein the electrode(s) is (are) embedded,
  a mechanoelectrical transducer for converting variations in the mechanical properties of the microbeam into an electrical signal, when the biological molecule A is brought into contact with a biological molecule B to be detected and/or quantified.

Nonlimiting examples of molecule A-molecule B pairings are the following:
  molecule A: antibody-molecule B: antigen.

Detection of a particular antigen by a particular antibody makes it possible to know, for example, whether or not a medium contains a particular antigen, for example for determining whether or not the medium is contaminated with the antigen of the contaminant;
  molecule A: DNA or RNA-molecule B: complementary strand;
  molecule A: sugar-molecule B: protein;
  molecule A: protein-molecule B: nucleic acid (DNA, RNA);
  molecule A: nucleic acid (DNA, RNA)-molecule B: protein;
  molecule A: protein-molecule B: protein;
  molecule A: antigen-molecule B: antibody.

The detection of a particular antibody makes it possible, for example, to determine whether a human or animal subject has already had the disease for which the antigen is the marker;
  molecule A: protein-molecule B: antibody or another protein.

The detection of a particular antibody by a particular protein makes it possible, for example, to detect certain markers for cancer, for Alzheimer's disease, etc.

In this context, the biosensor can also be used to screen for medicaments when the molecule A is an enzyme specific for a disease and when the molecule B is, for example, an inhibitor of this enzyme.

Thus, the possibilities for using the biosensor according to the invention are very broad.

The invention provides a process for the fabrication of a biosensor comprising:
  a microbeam, which is the mobile part of the biosensor, connected to a support,
  at least one electrode, at least one part of which is embedded in the microbeam, the electrode(s) optionally comprising a pad made of a ferromagnetic material,
  at least one biological molecule A grafted onto the microbeam in a zone different than the zone wherein the electrode(s) is (are) embedded,
  a mechanoelectrical transducer for converting variations in the mechanical properties of the microbeam into an electrical signal, when the biological molecule A is brought into contact with a biological molecule B to be detected and/or quantified,
  characterized in that:
  the microbeam and its support are made of a fluoropolymer material and form an integral component,
  and in that it comprises the following steps:
  a) formation of at least one electrode on a sheet made of a fluoropolymer material, wherein the interface between the fluoropolymer and the electrode is preferentially of covalent nature,
  b) optionally, formation of a pad made of a ferromagnetic material, on a zone of the electrode(s),
  c) passivation of the electrode(s),
  d) creation of the final desired shape of the biosensor in the sheet made of a fluoropolymer material and separation of this shape from the sheet,
  e) optionally, prefunctionalization of a zone of the microbeam, this zone being different than the zone wherein the electrode(s) is (are) embedded,
  f) functionalization either of the zone prefunctionalized in step e), when this step is carried out, or of a zone of the microbeam, this zone being different than the zone wherein the electrode(s) is (are) embedded, g) grafting of at least one biological molecule A onto the functionalized zone obtained in step f).

This combination of steps wherein the bonds between the electrodes and the fluoropolymer material, the bonds between the functionalized zone and the fluoropolymer material and the bonds between the functionalized zone and the molecule A are of covalent nature makes it possible to obtain a biosensor which has a lifetime and a sensitivity which are improved compared with the biosensors, having a size of about a few tens of microns, of the prior art, in which the electrodes and the functionalization of the microbeam are carried out respectively by physical deposition and via weak chemical bonds, creating interactions of physisorption type, characterized by weak adhesion of the materials.

The known methods for creating covalent interfaces made of a polymer material were thus far used only for devices having a size of a few tens of centimeters or millimeters.

Furthermore, no method for forming the structure of the biosensor and for release from the sheet made of a fluoropolymer material was known.

The electrode may be made of any conductive material which will become apparent to those skilled in the art.

Preferably in the invention, it will be made of copper or of gold.

Step d) of creation of the final desired shape of the biosensor in the sheet made of a fluoropolymer material and of separation of this shape from the sheet can be carried out:
  either after step c) of passivation of the electrodes,
  or after step e) of prefunctionalization when such a step e) is carried out,
  or after step f) of functionalization,
  or after step g) of grafting of the biomolecule A.

The preferred embodiments in the invention are those in which step d) is carried out before step g) of grafting of the biomolecule A, since they make it possible not to damage or otherwise affect the biological molecule A during this step d).

In this case, several methods can be implemented in order to carry out step d).

A first of these methods comprises the following steps:
  d1) fabrication of a cutting mold which is hollow or is in the shape of the structure of the desired final sensor,
  d2) compression of the mold fabricated in step d1) on the sheet made of a fluoropolymer material,
  d3) cutting of the desired structure around the mold by stamping with heating and/or ultrasonic acoustic excitation of the cutting mold.

A second method for carrying out step d) comprises a step d4) of cutting of the desired shape in the sheet made of a fluoropolymer material, by means of an excimer material laser emitting in the VUV wavelength range.

Inspiration may be drawn from the technique by fluoropolymer ablation with a VUV laser source of D. Riedel et al., Appl. Phys. A 69, 375-380 (1999).

A third method for carrying out step d) comprises the following steps:
  d5) deposition of a mask or of a stencil comprising an opening silhouetting the desired final shape of the sensor on the sheet made of a fluoropolymer material, and
  d6) cutting, by deep reactive-ion etching (DRIE), of the outlines of the opening of the mask or of the stencil.

For step d6), inspiration may be taken from the protocols established by E. Edqvist et al., J. Micromech. Microeng. 18, 015007 (2008) and Frank D. Egitto, Pure & Appl. Chem. 62(9), 1699-1708 (1990).

However, in the process of the invention, step d) may also be carried out only after steps f) of functionalization and g) of grafting of the biomolecule.

In this case, two particular methods will have to be applied.

These two particular methods can also be applied, of course, in the case where step d) is carried out before step e), after step e), or after step f).

Thus, a fourth method for carrying out step d) comprises the following steps:
  d7) fabrication of a cutting mold which is hollow or is in the shape of the structure of the desired final sensor,
  d8) compression of the mold fabricated in step d7) on the sheet made of a fluoropolymer material,
  d9) cutting of the desired structure around the mold by stamping of the mold at ambient temperature.

A fifth method for carrying out step d) comprises a step d10) of manual cutting, preferably with a scalpel, under a microscope, of the desired shape of the final sensor.

In the first and fourth methods, the mold may be made of any material having a hardness greater than that of the fluoropolymer material.

It will more particularly be made of copper or of silicon or of nickel.

Various methods for forming the electrodes can be used.

A first method for fabrication of the electrodes comprises the following steps:
  a1) deposition or grafting of a mask made of a material which is not transparent to VUV radiation, comprising at least one opening or one zone made of a material which is transparent to VUV radiation, on the sheet made of fluoropolymer material, this opening or this zone having the desired shape of the electrode(s),
  a2) irradiation by said VUV radiation, under an inert gas, preferably nitrogen, of the sheet obtained in step a1),
  a3) removal of the mask,
  a4) grafting, by conventional chemistry, of acrylic acid molecules, so as to form a poly(acrylic acid) (PAA) polymer in the irradiated zones obtained in step a2),
  a5) binding of $Cu^{2+}$ ions, by chelation, onto the PAA grafted in step a4), and
  a6) reduction of the $Cu^{2+}$ ions into copper microparticles or nanoparticles, preferably in the presence of $NaBH_4$,
  a7) growth, on the zones containing the copper microparticles or nanoparticles, of a layer of copper or of gold, by means of a metalization bath.

In step a2), the irradiation by VUV radiation is carried out under an inert gas.

Argon or nitrogen can be used as inert gas.

Nitrogen will be preferred for reasons of cost.

Step a4), just like in the remainder of the text, all the steps of grafting of acrylic acid molecules, by conventional chemistry, on zones irradiated by VUV radiation, can be carried out with the following components and the following procedure:

After VUV irradiation, the irradiated zones are brought into contact with a solution containing acrylic acid which is then polymerized. The percentage of acrylic acid of this solution may range from 0.5% to 100%. The solutions will then be prepared by diluting the acrylic acid in ultrapure water or ethyl acetate, for example. Preferably, it will be necessary to take a solvent which solubilizes acrylic acid in order to obtain a single phase. Those skilled in the art may refer to French patent application FR 0 955 859 for further information.

When the dilutions are carried out in water, Mohr's salt $((NH_4)_2Fe(SO_4)_2 \cdot 6H_2O)$ will be added in the amount of 0.25% by weight. Said salt makes it possible to inhibit homopolymerization of the acrylic acid in solution and therefore to promote the grafting onto/in the irradiated material.

Step a5), just like in the remainder of the text, all the steps of binding of $Cu^{2+}$ ions, by chelation, onto the PAA, and also step a6), of reducing these $Cu^{2+}$ ions, are completely described in patent application US 2010/0310800 filed on Apr. 30, 2010.

Step a5), just like in the remainder of the text, all the steps of binding of $Cu^{2+}$ ions, by chelation, can be carried out with the following compounds and according to the following procedure:

The step of binding of $Cu^{2+}$ ions of the process according to the present invention consists in placing the compound of polymer type capable of chelating (or complexing) metal ions in the presence of such metal ions.

In this case, poly(acrylic acid) polymer, i.e. poly(acrylic acid) or PAA, is preferentially used as compound of polymer type.

This step is therefore a step of chelation with complexation.

In the context of the present invention, the term "metal ion" is intended to mean an ion of $M^{n+}$ type, with M representing a metal and n an integer between 1 and 7, and generally between 1 and 4. Typically, it is an ion of an alkali metal, of an alkaline-earth metal, of a poor metal (in particular Al, Ga, In, Sn, Pb, Tl, Bi) or of a transition metal. The present invention relates more particularly to transition metal ions. Advantageously, a metal ion according to the invention is chosen from the group consisting of $Ag^+$, $Ag^{2+}$, $Ag^{3+}$, $Au^+$, $Au^{3+}$, $Cd^{2+}$, $Co^{2+}$, $Cr^{2+}$, $Cu^+$, $Cu^{2+}$, $Fe^{2+}$, $Hg^{2+}$, $Mn^{2+}$, $Ni^{2+}$, $Pd^+$, $Pt^+$, $Ti^{4+}$ and $Zn^{2+}$. During this step, the preferred ion is $Cu^{2+}$.

During this step of the process according to the invention, the metal ion is in a saline solution $S_1$, advantageously in an aqueous saline solution, in the presence of an anionic counterion. By way of usable anionic counterions, mention may be made of a chloride ($Cl^-$), a bromide ($Br^-$), a fluoride ($F^-$), an iodide ($I^-$), a sulfate ($SO_4^{2-}$), a nitrate ($NO_3^-$) or a phosphate ($PO_4^{3-}$).

It may be necessary to control the pH of the saline solution used during step (a5), in particular so that the groups (or structures) capable of chelating the metal ions borne by the compound of polymer type are in a form appropriate for this chelation, for example in an ionized form. Those skilled in the art will know, depending on the chelating groups borne by the compound of polymer type and on the solution $S_1$, whether or not it is necessary to modify the pH of this solution. If this is the case, those skilled in the art know various acid/base pairings capable of modifying the pH, such as $CH_3COOH/NH_3$ or $CH_3COOH/NaOH$.

Finally, the chelation step can be carried out with agitation, in particular using a stirrer, a magnetic bar, an ultrasonic bath or a homogenizer, and at a temperature below 60° C., especially between 5 and 50° C., and in particular between 10 and 40° C. Step a5) according to the invention is carried out, in a more particular embodiment, at ambient temperature. The term "ambient temperature" is intended to mean a temperature of 20° C.±5° C.

Step a6), of reduction of the $Cu^{2+}$ ions into copper microparticles or nanoparticles, is well known to those skilled in the art.

This step a6), like all the steps in the remainder of this text, which are steps of chemical or photochemical reduction of metal ions, can be carried out in the following way:

The step of chemical or photochemical reduction of the process according to the invention consists in reducing the metal ions chelated (or complexed) by the compound of polymer type. Any reduction technique known to those skilled in the art is usable during this step. Advantageously, this reduction step is a chemical reduction or a photoreduction. When this step is a step of chemical reduction, the latter uses a reducing solution $S_2$. Advantageously, the reducing solution $S_2$ is basic. The reducing solution $S_2$ comprises a reducing agent, in particular chosen from the group consisting of sodium borohydride ($NaBH_4$), dimethylaminoborane (DMAB—$H(CH_3)_2NBH_3$) and hydrazine ($N_2H_4$). When the reducing agent is $NaBH_4$, the pH of the reducing solution $S_2$ is neutral or basic, whereas, for DMAB, the pH of the solution $S_2$ is basic. The reducing agent is present in the reducing solution $S_2$ at a concentration of between $10^{-4}$ and 5 M, especially between 0.01 and 1 M, and in particular of about 0.1 M (i.e. 0.1 M±0.01 M). The chemical reduction step can be carried out at a temperature of between 30 and 90° C., especially between 40 and 80° C., and in particular between 50 and 80° C. Furthermore, step a6) of chemical reduction can last between 30 sec and 1 h, especially between 1 and 30 min and in particular between 2 and 20 min.

This step can be a photoreduction step. Typically, $Ag^+$, $Pt^+$, $Pd^+$ and $Au^+$ ions can be reduced by UV irradiation (Redjala T et al., New Journal Of Chemistry, Vol. 32, Issue 8, 2008; Eda Ozkaraoglu, Ilknur Tunc and Sefik Suzer, Polymer, Vol. 50, Issue 2, 2009). Generally, this reduction involves an intermediate which can typically be a counterion or an organic molecule which, when subjected to UV irradiation, gives the electrons required for the reduction of the metal ions. Furthermore, this type of process can involve linear optic and nonlinear optic phenomena (typically a multiphoton process). The use of a laser can make it possible to obtain nanostructuring or microstructuring of the metal deposit (Tanaka T, Ishikawa A, Kawata S, Applied Physics Letters, Vol. 88, Issue 8, 2006; Kaneko K, Sun H B, Duan X M, Kawata S, Applied Physics Letters, Vol. 83, Issue 7, 2003). This photoreduction is advantageously carried out in a solution $S_3$. The various characteristics and properties of the solution $S_2$ as previously defined also apply to the solution $S_3$.

It should be noted that carrying out a single step of binding of $Cu^{2+}$ ions and a single step of reducing these ions may not be sufficient to achieve the desired metalization. In this case, at least one further cycle with a further step a5) and a further step a6) should be carried out. It is possible to envision carrying out, after the 1st chelation/reduction cycle, from 1 to 20 additional cycles, in particular from 1 to 15 additional cycles, and in particular from 1 to 10 additional cycles. The term "additional cycle" is intended to mean a step a5) followed by a step a6).

It should also be emphasized that, despite several chelation/reduction cycles, it is possible for there to be no formation of a metal, but only formation of a form that is more reduced than that of the metal ion, namely a metal oxide. This variant depends on the metal considered, on the conditions during the reduction steps and on the environment, in particular on the presence of oxygen. A suitable choice of the conditions (redox potential of the reducing agent in the context of the chemical reduction, for example) makes it possible to obtain the type of metal entity desired. By modulating the experimental conditions, it is thus possible to obtain metalized substrates comprising various metal entities: metal or metal oxide and also metal ions.

The process for carrying out steps a5) and a6), and also all the steps which, in the remainder of the text, relate to a step of binding of $Cu^{2+}$ ions, by chelation, onto PAA and their chemical reduction, is described more completely in patent application FR 0 952 891.

Step a7), just like all the steps which, in the remainder of the text, are steps of growth or formation of a layer of copper or of gold, can be carried out according to the following procedure:

This step uses a metalization bath in which the activated polymers are immersed. In this bath, the metal growth is catalyzed by the metal particles deposited in step a6). The metalization bath is a stable solution containing at least one metal cation and its complexing agent, a reducing agent and a stabilizer, generally in an alkaline medium. The precursors of the metal material which are reduced in step a6) of the process according to the invention have predominantly an oxidation state of 0.

Thus, the metalization can then take place by immersion in a metalization bath and growth on the particles of precursors with an oxidation state of 0.

For the metalization in order to form a layer of copper, the samples are immersed in the solution described in table 1 hereinafter, heated to 40° C. in a water bath:

TABLE 1

Composition of the copper metalization bath
Metalization bath

| Reagents | w(g) for 100 ml | C (g/l) |
|---|---|---|
| $CuSO_4 \cdot 7H_2O$ | 0.5 | 5 |
| Disodium tartrate $C_4H_4Na_2O_6$ | 2.96 | 25 |
| NaOH | 0.5 | 7 |
| Formaldehyde HCHO (37% in $H_2O$) | 2.94 | 10 ml/l |

After 15 min, the samples were rinsed with ultrapure water, for example provided by the company Millipore, with ultrasound for 10 min before being dried.

Infrared analysis reveals the disappearance of the peaks of the various polymers.

XPS analysis confirms the presence of a layer of copper metal (in its reduced form, $Cu^0$). The copper layer is also visible to the naked eye. The presence of carbon, nitrogen and oxygen after metalization is due to the presence of organic impurities at the extreme surface of the metalized substrate. The oxygen can also come from oxidation in air of the copper layer before the analysis.

In this method, a mask made of a material which is not transparent to VUV radiation, comprising either one or more openings, or one or more zones made of a material that is transparent to VUV radiation, is used.

As material which is not transparent to VUV radiation, mention may be made of copper and silicon, and as material which is transparent to VUV radiation, mention may be made of fused silica, quartz, $CaF_2$ and $MgF_2$.

The electrodes can also be fabricated according to the method comprising the following steps:

a8) deposition of a layer of positive-type resin, sensitive to UV radiation, on the sheet made of a fluoropolymer material, a9) irradiation, with said UV radiation, of the layer formed in step a8) through a mask made of a material which is not transparent to said UV radiation, comprising at least one opening or one zone made of a material which is transparent to said UV radiation, this opening or this zone having the desired shape of the electrode(s), a10) elimination of the irradiated resin and of the mask, a11) formation of a PAA polymer, in the zones where the resin has been eliminated, via diazonium salt technology, a12) binding of $Cu^{2+}$ ions, by chelation, onto the PAA formed in step a11), a13) reduction of the $Cu^{2+}$ ions chelated in the PAA so as to form copper microparticles or nanoparticles making it possible to autocatalyze the metalization bath of step a14), a14) growth, by means of a metalization bath, of a layer of copper or of gold on the zones comprising the copper microparticles or nanoparticles, a15) elimination of the remaining photosensitive resin.

In this method, a positive-type resin sensitive to UV radiation is used, and the irradiated resin zones are then eliminated after the irradiation.

However, a layer of negative-type photosensitive resin could also be used, but, in this case, the zones made of a material which is transparent to UV radiation, or the openings of the mask, will have to silhouette the desired shape of the electrode(s) and it is the nonirradiated resin zones that will be eliminated in step a10).

The mask used is a mask made of a material which is not transparent to UV radiation, comprising either openings (absence of material in this opening) or zones made of a material which is transparent to UV radiation.

Examples of materials which are not transparent to UV radiation are copper, silicon, certain inks, and certain polymer materials such as, for example, polyethylene terephthalate (PET) or polypropylene (PP).

Examples of materials which are transparent to UV radiation are fused silica, quartz, calcium fluoride ($CaF_2$), magnesium fluoride ($MgF_2$), glass or silica.

Step a11) is a step of formation of a PAA polymer via the diazonium salt technology. Diazonium salt technology is also known, in the art, as GraftFast® technology.

This step, like all the steps which, in the remainder of the text, refer to the grafting of acrylic acid molecules onto the sheet made of a fluoropolymer material, via diazonium salt technology, is carried out in the following way:

A solution of a diazonium salt is first of all prepared from 10 ml of a solution of 1,4-phenyldiamine at 0.1 M in HCl (0.5 M), to which 10 ml of a solution of $NaNO_2$ at 0.1 M in water have been added. 200 mg of iron filings and then, after 5 min, 10 ml of AA are added to this diazonium salt solution.

The sample is then introduced into the reaction medium for 2 h, before being rinsed with water and introduced into a sodium hydroxide solution at pH 9.5 in the presence of ultrasound so as to solubilize the ungrafted poly(acrylic acid) (PAA). Further details regarding this method will be found in French patent FR 2 910 006.

Step a) of fabrication of the electrodes can also be carried out according to a method which comprises the following steps:

a16) formation of a PAA polymer on the sheet made of a fluoropolymer material, via diazonium salt technology, a17) binding of $Cu^{2+}$ ions, by chelation, onto the PAA formed in step a16), a18) reduction of the chelated ions in order to form copper microparticles or nanoparticles for activating the metalization bath of step a19), a19) growth, by means of a metalization bath, of a layer of copper or of gold on the zones comprising the copper microparticles or nanoparticles, a20) deposition of a layer of positive-type resin, sensitive to UV radiation, on the surface of the sheet made of fluoropolymer material and which has been metalized, obtained in step a19), a21) irradiation, with said UV radiation, of the layer formed in step a20), through a mask made of a material which is not transparent to said UV radiation, comprising at least one opening or one zone made of a material which is transparent to said UV radiation, this opening or this zone silhouetting the desired shape of the electrode(s), a22) elimination of the irradiated resin, a23) elimination of the copper or of the gold, by chemical etching, preferably with $FeCl_3$ when the layer formed in step a19) is made of copper, or with an $HNO_3/HCl$ mixture (aqua regia), when the layer formed in step a19) is made of gold, in the zones where the resin has been eliminated, a24) elimination of the remaining photosensitive resin.

Step a17), of binding of $Cu^{2+}$ ions, by chelation, onto the PAA and reduction of these $Cu^{2+}$ ions, is completely described in patent application US 2010/0310800 filed on Apr. 30, 2010.

With regard to step a23), just like the steps which, in the remainder of the text, are steps of elimination, by chemical etching, of the layer of copper or of gold formed, it is carried out by dipping the sheet made of a fluoropolymer material either in an $FeCl_3$ solution, when the layer is made of copper, or in aqua regia, which is a mixture of concentrated nitric acid and hydrochloric acid containing two or three volumes of hydrochloric acid for one volume of nitric acid, when the layer is made of gold.

Step a) of formation of the electrodes can also comprise the following steps:

a25) irradiation of a sheet made of a fluoropolymer material with VUV radiation, under an inert gas, preferably nitrogen, a26) grafting, onto the sheet obtained in step a25), of acrylic acid molecules, by conventional chemistry, so as to form an acrylic acid polymer PAA, a27) binding of $Cu^{2+}$ ions, by chelation, onto the PAA grafted in step a26), a28) reduction of the $Cu^{2+}$ ions into copper microparticles or nanoparticles, preferably with $NaBH_4$, a29) growth, on the zones comprising the copper microparticles or nanoparticles, of a layer of copper or of gold, by means of a metalization bath, a30) deposition of a layer of positive-type resin, sensitive to UV radiation, on the metalized sheet made of a fluoropolymer material, obtained in step a29), a31) irradiation, with said UV radiation, of the layer formed in step a30), through a mask made of a material which is transparent to said UV radiation, comprising an opening or a zone made of a material which is transparent to UV radiation, this opening or this zone silhouetting the desired shape of the electrode(s), a32) elimination of the irradiated resin and of the mask, a33) elimination, by chemical etching, in the zones where the resin has been irradiated, of the layer of copper if formed in step a29), preferably with $FeCl_3$, or of the layer of gold, if formed in step a29), preferably with an $HNO_3/HCl$ mixture (aqua regia), a34) elimination of the remaining resin.

Finally, a last method for carrying out step a) of formation of the electrodes, in the process of the invention, is a step which comprises the following steps:

a35) deposition of a layer of positive-type resin, sensitive to UV radiation, on the surface of the sheet made of fluoropolymer material, a36) irradiation, with said UV radiation, of the layer formed in step a35), through a mask made of a material which is not transparent to UV radiation, comprising at least one opening or one zone made of a material which is transparent to said UV radiation, this opening or zone having the desired shape of the electrodes, a37) elimination of the zones of irradiated resin and of the mask, a38) deposition of gold in the zones in which the resin has been eliminated, by physical evaporation under vacuum, preferably by plasma or heating, or spraying, a39) elimination of the remaining photosensitive resin.

Once the electrode is formed, and when it is desired to form a pad made of ferromagnetic material on this electrode, step b) of formation of a pad made of a ferromagnetic material will then be carried out.

When a pad made of ferromagnetic material on the electrodes is not necessary, the process will go directly to step c) of passivation of the electrodes.

Step b) of formation of a pad made of a ferromagnetic material can be carried out by means of a method which comprises the following steps:

b1) deposition of a layer of positive-type resin, sensitive to UV radiation, on the sheet made of a fluoropolymer material comprising the electrodes, b2) deposition or grafting of a mask made of a material which is not transparent to said UV radiation, comprising an opening or a zone made of a material which is transparent to said UV radiation, this opening or this zone having the shape and the location, on the sheet obtained in step b1), of the desired pad, on a zone of the electrode previously obtained by means of the steps a), b3) irradiation, by said UV radiation, of the sheet obtained in step b2), b4) elimination of the irradiated photosensitive resin and of the mask, b5) formation of a PAA polymer in the zones where the irradiated resin has been eliminated, via diazonium salt technology, b6) binding, by chelation, of metal ions chosen from $Ni^+$, $Fe^{2+}$, $Fe^{3+}$ and $Co^{2+}$ or of a mixture of at least two of them, onto the PAA grafted in step b5), b7) reduction of the metal ions bound in step b6), b8) optionally, growth of the resulting metal layer, b9) elimination of the remaining photosensitive resin.

Step b5) of formation of a PAA polymer in the zones where the irradiated resin has been eliminated, via diazonium salt technology, corresponds to the implementation of GraftFast® technology which is completely described in patent application FR 0 758 660 and also above.

With regards to step b7) of chemical reduction of the metal ions bound in step b6), it is carried out as previously.

Step b8), just like all the steps which, in this text, refer to a step of growth of the metal layer, can be carried out using the following compounds and in the following way:

electroplating bath containing, for a controlled deposition of permalloy (NiFe):

$NiSO_4.6H_2O$ at 0.7 mol/l
$FeSO_4.7H_2O$ at 0.03 mol/l
$NiCl_2.6H_2O$ at 0.02 mol/l
$H_3BO_3$ at 0.4 mol/l
Saccharin at 0.016 mol/l with a pH of 2.3 and a temperature of 40° C.

The electrode of the fluoropolymer sheet, dipped in this bath, is connected to a source of current with a carbon counterelectrode in the same bath for a current density of 14.5 $mA/cm^2$. This electroplating will preferentially be carried out under an external magnetic field (of about 0.2 milliTesla) applied in order to improve the magnetic properties of the ferromagnetic pad for the magneto-impedance sensor.

This step is carried out when the thickness of the metal layer obtained after reduction of the metal ions is not sufficient, i.e. at a thickness of less than 1 micrometer.

Step c) of passivation of the electrodes, according to a first embodiment, comprises the following steps:

c1) spin-coating of SU8® negative-type epoxy resin onto the sheet made of a fluoropolymer material comprising the electrodes, c2) deposition or grafting, onto the layer of resin obtained in step c1), of a mask made of a material which is not transparent to UV radiation, comprising an opening or a zone made of a material which is transparent to said UV radiation, this opening or this zone having the shape of the electrode(s), c3) irradiation, with said UV radiation, of the layer of SU8® resin through the mask, c4) elimination of the mask and of the nonirradiated resin, c5) curing under annealing, between 70° C. and 120° C. for 1 minute, of the remaining resin.

The nonirradiated zones of SU8® resin, sold by the company MicroChem. Corp. (Newton, USA), are eliminated with the PGMEA (propylene glycol monomethyl ether acetate) revealing agent.

Step c) of passivation of the electrodes can also be carried out by means of a method which comprises the following steps:

c6) deposition of a layer of positive-type resin, sensitive to UV radiation, on the sheet made of a fluoropolymer material comprising the electrodes, c7) irradiation, with said UV radiation, of the layer of sensitive resin through a mask made of a material which is not transparent to said UV radiation, comprising an opening or a zone made of a material which is not transparent to said UV radiation, this opening or zone having the shape of the electrode(s), c8) removal of the mask and elimination of the irradiated resin, c9) pyrolytic deposition of a layer of type N parylene ([2,2]-paracyclophane) or type C parylene (chloro-[2,2]-paracyclophane) in the zones where the resin has been eliminated, c10) elimination of the remaining resin sensitive to UV radiation.

However, this step c) of passivation of the electrodes can also be carried out according to a method which comprises the following steps:

c11) electrografting of an electrophoretic polymer material onto the electrodes, c12) curing of the electrophoretic polymer material by heating.

The electrophoretic polymer material which is electrografted in step c11) is, for example, a Glassophor® cathodic electrophoretic paint (BASF, Germany).

The electrografting is carried out in the following way:

The electrode to be passivated with a film of electrophoretic paint is connected to the negative pole of a voltage source, and dipped in a bath of Glassophor®.H$_2$O at 40% with a platinum counterelectrode connected to the positive pole of the voltage source. A voltage of 17 volts is then applied between the two electrodes until the current detected in the circuit becomes zero. The electrode coated with the passivating film is then removed from the bath and rinsed with Millipore® ultrapure water.

The heating in step c12) is carried out at a temperature of between 70° C. and 130° C. for approximately 30 minutes.

The purpose of the functionalization step f) is to provide a zone of the microbeam with functions capable of reacting with functions of the biomolecule A, so as to allow grafting of the biomolecule A.

When the function capable of reacting with a function of the biomolecule A is a carboxylic acid function (COOH), step f) is, in the invention, a step of formation of a layer of poly(acrylic acid) polymer PAA.

In this case, the process of the invention does not comprise a prefunctionalization step e), and two methods of functionalization (formation of a layer of PAA polymer) are possible.

The first of these methods comprises the following steps:

f1) deposition or grafting of a mask made of a material which is not transparent to VUV radiation, comprising an opening or a zone made of a material which is transparent to said VUV radiation, this opening or this zone having the shape of the zone of the sheet made of a fluoropolymer material to be functionalized, this opening or this zone being located in the part of the mask corresponding to the microbeam to be formed, and outside the zone of the microbeam in which the electrode(s) is (are) embedded or to be embedded, f2) irradiation, by said VUV radiation, under an inert gas, preferably nitrogen, of the sheet obtained in step f1), f3) removal of the mask, f4) formation, by conventional chemistry, of a poly(acrylic acid) PAA polymer, in the irradiated zones.

Step f1) of grafting of a mask onto the fluoropolymer sheet can be carried out by applying a mask made of a material which is not transparent to VUV radiation, comprising either one or more openings, or one or more zones made of a material which is transparent to VUV radiation. As material which is not transparent to VUV radiation, mention may be made of copper or silicon, and as material which is transparent to VUV radiation, mention may be made of fused silica, quartz, $CaF_2$ and $MgF_2$.

The second method for carrying out step f) comprises the following steps:

f5) deposition of a layer of positive-type resin, sensitive to UV radiation, on the sheet made of a fluoropolymer material, f6) irradiation, by said UV radiation, of the layer of sensitive resin through a mask made of a material which is not transparent to said UV radiation, comprising an opening or a zone made of a material which is transparent to said UV radiation, this opening or this zone having the shape of the zone to be functionalized and being located in the part of the mask corresponding to the microbeam part to be formed and outside the zone of the microbeam in which the electrode(s) is (are) embedded or to be embedded, f7) elimination of the irradiated resin and of the mask, f8) formation of an acrylic acid polymer (PAA), in the zones where the resin has been eliminated, via diazonium salt technology, f9) elimination of the remaining resin.

When, in order to graft the biomolecule A, it is necessary for a zone of the microbeam to have functions other than a carboxylic acid function, i.e. when, in order to graft the biomolecule A, it is necessary to have functions such as amine ($NH_2$) functions, thiol (SH) functions, azide ($N_3$) functions, alcohol (hydroxyl) (OH) functions, alkene functions or maleimide groups, or activated ester groups, preferably succinimide ester groups, the process of the invention comprises a step e) of prefunctionalization of a zone of the microbeam, this prefunctionalized zone then being modified by grafting of an organic molecule which will then bear the function or the group necessary for reacting with a group of the biological molecule.

In this case, a first method for carrying out prefunctionalization step e) comprises the following steps:

e1) deposition or grafting of a mask made of a material which is not transparent to VUV radiation, comprising an opening or a zone made of a material which is transparent to said VUV radiation, this opening or this zone having the shape of the zone of the sheet made of a fluoropolymer material to be functionalized, this opening or this zone being located in the part of the mask corresponding to the microbeam to be formed, and outside the zone of the microbeam in which the electrode(s) is (are) embedded or to be embedded, e2) irradiation, by said VUV radiation, under an inert gas, preferably nitrogen, of the sheet obtained in step e1), e3) removal of the mask, e4) formation of a poly(acrylic acid) PAA polymer, by conventional chemistry, in the irradiated zones.

A second method for carrying out prefunctionalization step e) comprises the following steps:

e5) deposition of a layer of positive-type resin, sensitive to UV radiation, on the sheet made of a fluoropolymer material, e6) irradiation, by said UV radiation, of the layer of sensitive resin through a mask made of a material which is not transparent to said UV radiation, comprising an opening or a zone made of a material which is transparent to said UV radiation, this opening or this zone having the shape of the zone to be functionalized and being located in the part of the mask corresponding to the microbeam part to be formed and outside the zone of the microbeam in which the electrode(s) is (are) embedded or to be embedded, e7) elimination of the irradiated resin and of the mask, e8) formation of an acrylic acid polymer (PAA), in the zones where the resin has been eliminated, via diazonium salt technology, and e9) elimination of the remaining resin.

Step f) of functionalization of the zones which have been prefunctionalized by means of the first and second method of prefunctionalization described above is then a step, denoted f10), of modification of the PAA polymer formed in step e4) or in step e8) with an organic molecule comprising, at its end not bonded to the PAA, $NH_2$, SH, $N_3$, OH or alkene functions, or maleimide groups, or activated ester groups, preferably succinimide ester groups, by conventional chemistry, in the zone irradiated in step e6).

As previously, this modification of the PAA is carried out by conventional chemistry; the PAA is modified with an organic molecule either by creation of an amide bond, for example, between a carboxylic acid function of the PAA and a primary or secondary amine function of the organic molecule, or by creation, for example, of an ester bond between a carboxylic acid function of the PAA and an alcohol of the organic molecule. The organic molecule thus grafted may then exhibit another function or a group which can be functionalized or can react with a biological molecule. This function or this group may be an amine $NH_2$ function, a thiol SH function, an azide $N_3$ function, an alcohol (hydroxyl) function, a terminal alkene function, a maleimide group, or an activated ester group of the succinimide ester type. Those skilled in the art will be capable of modifying the PAA accordingly, in order to be able to functionalize it with such an organic molecule.

When step g) of grafting of the biomolecule A is carried out by reacting the reactive functions of the biomolecule A with diazonium functions present on the zone of the microbeam, prefunctionalization step e) comprises the following steps:

e10) deposition of a layer of positive-type resin, sensitive to UV radiation, on the sheet made of a fluoropolymer material, e11) irradiation, by said UV radiation, of the layer of sensitive resin through a mask made of a material which is not transparent to said UV radiation, comprising an opening or a zone made of a material which is transparent to said UV radiation, this opening or this zone having the shape of the zone to be functionalized, and being located in the part of the mask corresponding to the microbeam to be formed, but outside the zone of the microbeam in which the electrode(s) is (are) embedded or to be embedded, e12) elimination of the irradiated resin, e13) removal of the mask, e14) grafting of a layer of poly(aminophenylene) polymer onto the zone where the resin has been eliminated.

In this case, functionalization step f) is a step f11) of activation of the layer of poly(aminophenylene) polymer formed in step e14) to give a layer of poly(diazonium phenylene).

In order to carry out step e14), use may be made of the following starting compounds and the following protocol:

The primer was prepared according to the protocol which was shown in [Chem. Mater. 2007, 19, 6323-6330].

Samples were immersed for 40 min in a mixture comprising 2 ml of an aqueous solution of $NH_2$-Ph-$NH_2$ ($5 \times 10^{-3}$ M in 0.5 M HCl), 2 ml of an aqueous solution of $NaNO_2$ ($5 \times 10^{-3}$ M) and 80 mg of iron filings. Unlike the Chem. Mater. 2007, 19 6323-6330 protocol, the reaction is carried out in this case at 35° C. in order to obtain thicker films.

Strips of polyvinylidene fluoride (PVDF)β membranes (1 cm×4 cm and 25 μm thick) were immersed for 120 min in a mixture comprising 2 ml of an aqueous solution of $NH_2$-Ph-$NH_2$ ($5 \times 10^{-3}$ M in 0.5 M HCl), 2 ml of an aqueous solution of $NaNO_2$ ($5 \times 10^{-3}$ M) and 80 mg of iron filings. Ulike the Chem. Mater. 2007, 19, 6323-6330 protocol, the reaction is carried out in this case at 35° C. in order to obtain thicker films.

Step f11), just like all the steps which, in the remainder of the text, are steps of modification of a layer of polymer of the poly(aminophenylene) type to give poly(diazonium phenylene), is described in patent application FR 0 857 260.

In order to carry it out, use may be made of the following starting compounds and the following protocol:

The primer-coated surfaces were immersed in an aqueous solution of 0.5 M HCl and of $5 \times 10^2$ M $NaNO_2$. During this step, the $NaNO_2$ concentration does not need to be precise, there is always an excess relative to the amine functions present at the surface.

The formation of the diazonium salts could be followed by IR spectrometry: a peak at 2270 cm$^{-1}$ corresponding to the diazonium. The reaction carried out here can be represented diagrammatically in the following way:

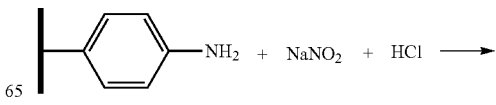

In aqueous medium

-continued

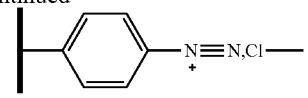

For further information, those skilled in the art may refer to French patent application No. 0 857 269.

When the surface is covered with an active layer of poly(diazonium phenylene), the protocol for grafting of the molecule A is the following:

Low-molecular-weight salmon sperm DNA (Fluka) was dissolved in ultrapure water, for example supplied by the company Millipore (1 mg in 3 ml). 200 μl of this solution were deposited on the sample covered beforehand with a layer of poly(diazonium phenylene). The deposition was carried out without specific precautions and at ambient temperature. After 10 min of reaction, the support is rinsed with Millipore ultrapure water and then subjected to washing with sonication: Millipore® ultrapure 2 min/ethanol 2 min/Millipore® ultrapure 2 min.

The appearance of bands at 1226 cm$^{-1}$ and at 1080 cm$^{-1}$ on the support comprising the activated self-adhesive layer confirms the presence and the covalent grafting of DNA at the surface.

Glucose oxidase (Sigma Aldrich) was dissolved in ultrapure water (1 mg in 3 ml). 200 μl of this solution were deposited on the sample covered beforehand with a layer of poly(diazonium phenylene). The deposition was carried out without specific precautions and at ambient temperature. After 10 min of reaction, the support is rinsed with ultrapure water and then subjected to washing with sonication: ultrapure water 2 min/ethanol 2 min/ultrapure water 2 min.

The appearance of bands at 1659 cm$^{-1}$ (Amide I), at 1546 cm$^{-1}$ (Amide II) and at 1255 cm$^{-1}$ (Amide III) on the support comprising the activated self-adhesive layer confirms the presence and the covalent grafting of glucose oxidase at the surface.

However, a fourth method and a fifth method of prefunctionalization of a zone of the microbeam can also be used when, in order to graft the biomolecule A onto the microbeam, it is necessary for this zone of the microbeam to have functions other than carboxylic acid functions.

Thus, a fourth method for carrying out prefunctionalization step e) comprises the following steps:

e15) deposition or grafting, onto the sheet made of a fluoropolymer material, of a mask, made of a material which is not transparent to VUV radiation, comprising an opening or a zone made of a material which is transparent to said VUV radiation, this opening or this zone having the desired shape of the zone to be functionalized, and being located in the zone of the mask corresponding to the microbeam to be formed but different than that in which the electrode(s) is (are) embedded or to be embedded, e16) irradiation, by said VUV radiation, under an inert gas, of the sheet obtained in step e15), e17) removal of the mask, e18) formation, by conventional chemistry, of a layer of an acrylic acid polymer (PAA) in the irradiated zones obtained in step e16), e19) binding of Cu$^{2+}$ ions, by chelation, onto the PAA grafted in step e18), e20) growth, in the zone where the Cu$^{2+}$ ions were bound, of a layer made of a metal chosen from copper, gold, platinum or silver, by reduction of the Cu$^{2+}$ ions when the layer to be formed must be made of copper, or in a metal bath, when the layer to be formed must be made of a metal other than copper.

The fifth method for carrying out prefunctionalization step e) comprises the following steps:

e21) deposition of a layer of positive-type resin, sensitive to UV radiation, on the sheet made of a fluoropolymer material, e22) irradiation, with said UV radiation, of the layer formed in step e21), through a mask made of a material which is not transparent to said UV radiation, comprising an opening or a zone made of a material which is transparent to said UV radiation, this opening or this zone having the desired shape of the zone to be functionalized, and being located in the zone of the mask corresponding to the microbeam to be created but different than that in which the electrode(s) is (are) embedded or to be embedded, e23) elimination of the irradiated resin and removal of the mask, e24) grafting of a layer made of a PAA polymer, via diazonium salt technology, in the zones where the resin has been eliminated, e25) binding of Cu$^{2+}$ ions, by chelation, onto the PAA grafted in step e24), in the zones where the resin has been eliminated, e26) growth, in the zone where the Cu$^{2+}$ ions were bound, of a layer made of a metal chosen from copper, gold, platinum or silver, by reduction of the Cu$^{2+}$ ions, when the layer is made of copper, or in a metal bath when the layer is made of a metal other than copper, e27) elimination of the remaining resin.

Step f) of functionalization of the zone of the microbeam which has been functionalized by means of the fourth and fifth methods of prefunctionalization depends, here again, on the function that it is necessary to graft onto the prefunctionalized zone so that it reacts with a reactive function of the biomolecule A.

Thus, when the biomolecule A is grafted by means of a reactive function which reacts with a diazonium function of the desired zone of the microbeam, functionalization step f) comprises the following steps:

f12) deposition of a positive-type resin, sensitive to UV radiation, on the sheet comprising the metalized zone obtained in step e20) or on the sheet comprising the metalized zone obtained in step e26), f13) irradiation of the sheet obtained in step f12), through a mask made of a material which is not transparent to said UV radiation, comprising an opening or a zone made of a material which is transparent to said UV radiation, this opening or this zone corresponding to the metalized zone of the sheet other than the electrode(s) defined in the protocols a), f14) elimination of the irradiated resin and of the mask, f15) grafting of a layer of poly(aminophenylene) polymer onto the zone where the resin has been eliminated, f16) elimination of the remaining resin, f17) activation of the layer of poly(aminophenylene) to give a layer of poly(diazonium phenylene).

This method of functionalization is applicable regardless of the nature of the metal layer which has been grown in step e20) or in step e26), respectively.

A specific method of prefunctionalization of the prefunctionalized (metalized) zones, using the fourth and fifth methods of prefunctionalization of the invention, when these zones are made of gold, is a method which comprises the following steps:

f18) creation of a self-assembled alkanethiol/Au layer on a metalized zone of the sheet, different than that or those where the electrode(s) has (have) been formed by means of the steps a), f19) bonding of the free part of the molecule corresponding to the alkanethiol of the self-assembled monolayer obtained in step f24) with an organic molecule comprising $NH_2$, SH, $N_3$, OH or alkene reactive free end functions, or maleimide, or activated ester, preferably succinimide ester, free end groups.

The biomolecule A is grafted onto the reactive free end groups and functions of the molecule bonded in step f19).

Finally, a particular method of functionalization f) when the functionalized (metalized) zones obtained by means of the prefunctionalization methods e), according to the invention, are made of a metal other than gold, is a method which comprises the following steps:

f20) deposition of a positive-type resin, sensitive to UV radiation, on the sheet comprising the metalized zone obtained in step e20) or on the sheet comprising the metalized zone obtained in step e26), f21) irradiation of the sheet obtained in step f20), through a mask made of a material which is not transparent to said UV radiation, comprising an opening or a zone made of a material which is transparent to said UV radiation, this opening or this zone corresponding to the metalized zone of the sheet other than the electrode(s) defined in the protocols a), f22) elimination of the irradiated resin and of the mask, f23) formation, via diazonium salt technology, in the zone irradiated in step f21), of a polymer obtained by polymerization of monomers comprising vinyl or acrylate functions, f24) elimination of the remaining resin, f25) modification, by conventional chemistry, of the polymer formed in step f23) by reaction of the reactive groups of the polymer with the reactive groups of an organic molecule comprising $NH_2$, SH, $N_3$, OH or alkene free end functions, or maleimide or activated ester, preferably succinimide ester, free end groups.

The biomolecule A is then grafted onto these free reactive functions or groups of the organic biomolecule bound in step f25).

Generally, the functionalized microbeam zone, the molecule in step g) of grafting of the biomolecule A is a step of reaction of the reactive functions of the biomolecule A with the free reactive functions present on the functionalized zone of the microbeam.

The invention claimed is:

1. A process for the fabrication of a biosensor, said biosensor comprising:
   a microbeam, which is a mobile part of the biosensor, connected to a support,
   at least two electrodes, at least a part of each electrode being embedded in the microbeam,
   at least one biological molecule (A) grafted onto the microbeam in a location different from where said electrodes are embedded,
   a piezoelectric transducer for converting variations in the mechanical properties of the microbeam into an electrical signal, when the at least one biological molecule (A) is brought into contact with a biological molecule (B) to be detected and/or quantified, wherein the microbeam and its support are made of a fluoropolymer material and form an integral component,
   the process comprising the following steps:
   (a) formation of at least two electrodes on a sheet made of a fluoropolymer material,
   (b) passivation of the at least two electrodes,
   (c) creation of a final desired shape of the biosensor in the sheet made of a fluoropolymer material, said desired shape being defined by the microbeam and its support both made of said fluoropolymer material and forming an integral component as well as the at least two electrodes at least a part of each electrode being embedded in the microbeam and, separation of the final desired shape from the sheet,
   (d) optionally, prefunctionalization of a zone of the microbeam, the zone being at a location different from where the at least two electrodes are embedded,
   (e) functionalization of either the zone prefunctionalized in step (d), when step (d) is carried out, or of a zone of the microbeam, this zone being different than the zone wherein the at least one electrode is embedded,
   (f) grafting of at least one biological molecule (A) onto the functionalized zone obtained in step (d), and wherein step (a) further comprises the following steps:
   (a1) deposition or grafting of a mask made of a material which is not transparent to VUV radiation, comprising at least one opening or zone made of a material which is transparent to VUV radiation, on the sheet made of fluoropolymer material, this opening or zone having the desired shape of the at least two electrodes,
   (a2) irradiation by said VUV radiation, under an inert gas, of the sheet obtained in step (a1),
   (a3) removal of the mask,
   (a4) grafting of acrylic acid molecules, so as to form a poly(acrylic) acid (PAA) polymer in the irradiated zones obtained in step (a2),
   (a5) binding of $Cu^{2+}$ ions, by chelation, onto the PAA grafted in step (a4),
   (a6) reduction of the $Cu^{2+}$ ions into copper microparticles or nanoparticles,
   (a7) growth, on the zones containing the copper microparticles or nanoparticles, of a layer of copper or of gold, by means of a metalization bath.

2. The process as claimed in claim 1, wherein step (c) is performed between step (e) and step (f).

3. The process as claimed in claim 1, wherein step (c) is performed after step (f) of grafting.

4. The process as claimed in claim 1, further comprising step (d) and wherein step (c) is performed after step (d) and before step (e).

5. The process as claimed in claim 1, wherein step (a) further comprises the following steps:
   (a8) deposition of a layer of positive-type resin, sensitive to UV radiation, on the sheet made of a fluoropolymer material,
   (a9) irradiation, with said UV radiation, of the layer formed in step (a8) through a mask made of a material which is not transparent to UV radiation, comprising at least one opening or one zone made of a material which is transparent to said UV radiation, this opening or this zone having the desired shape of the at least two electrodes,
   (a10) elimination of the irradiated resin and of the mask,
   (a11) formation of a PAA polymer, in the zones where the resin has been eliminated, via diazonium salt technology,
   (a12) binding of $Cu^{2+}$ ions, by chelation, onto the PAA formed in step (a11),
   (a13) reduction of the chelated $Cu^{2+}$ ions so as to form copper microparticles or nanoparticles making it possible to autocatalyze the metalization bath of step (a14), (a14) growth, by means of a metalization bath, of a layer of copper or of gold on the zones comprising the copper microparticles or nanoparticles, (a15) elimination of the remaining photosensitive resin.

6. The process as claimed in claim 1, wherein step (a) further comprises the following steps:

(a16) formation of a PAA polymer on the sheet made of a fluoropolymer material, via diazonium salt technology, (a17) binding of $Cu^{2+}$ ions, by chelation, onto the PAA formed in step (a16), (a18) reduction of the chelated $Cu^{2+}$ ions into copper microparticles or nanoparticles, (a19) growth, by means of a metalization bath, of a layer of copper or of gold on the zones comprising the copper microparticles or nanoparticles, said metallization bath being activated by the reduction performed during step (a18), (a20) deposition of a layer of positive-type resin, sensitive to UV radiation, on the surface of the sheet made of fluoropolymer material and which has been metalized, obtained in step (a19), (a21) irradiation, with said UV radiation, of the layer formed in step (a20), through a mask made of a material which is transparent to said UV radiation, comprising at least one opening or one zone made of a material which is not transparent to said UV radiation, this opening or this zone silhouetting the desired shape of the at least two electrodes (a22) elimination of the irradiated resin and of the mask, (a23) elimination of the copper or of the gold, by chemical etching in the zones where the resin has been eliminated, (a24) elimination of the remaining photosensitive resin.

7. The process as claimed in claim 1, wherein step (a) further comprises the following steps:

(a25) irradiation of a sheet made of a fluoropolymer material with VUV radiation, under an inert gas, (a26) grafting, onto the sheet obtained in step (a25), of acrylic acid molecules so as to form an acrylic acid polymer PAA, (a27) binding of $Cu^{2+}$ ions, by chelation, onto the PAA grafted in step (a26), (a28) reduction of the $Cu^{2+}$ ions into copper microparticles or nanoparticles, (a29) growth, on the zones comprising the copper microparticles or nanoparticles, of a layer of copper or of gold, by means of a metalization bath, (a30) deposition of a layer of positive-type resin, sensitive to UV radiation, on the metalized sheet made of a fluoropolymer material, obtained in step (a29), (a31) irradiation, with said UV radiation, of the layer formed in step (a30), through a mask made of a material which is transparent to said UV radiation, comprising an opening or a zone made of a material which is not transparent to said UV radiation, this opening or this zone silhouetting the desired shape of the at least two electrodes, (a32) elimination of the irradiated resin and of the mask, (a33) elimination, by chemical etching, in the zones where the resin has been irradiated, either of the layer of copper if formed in step (a29), or of the layer of gold, if formed in step (a29), (a34) elimination of the remaining resin.

8. The process as claimed in claim 1, wherein step (b) further comprises the following steps:

(b1) spin-coating of SU-8-negative-type epoxy resin onto the sheet made of a fluoropolymer material comprising the at least two electrodes, (b2) deposition or grafting, onto the layer of resin obtained in step (c1), of a mask made of a material which is not transparent to said UV radiation, comprising an opening or a zone made of a material which is transparent to UV radiation, this opening or zone having the shape of the at least two electrodes, (b3) irradiation, with said UV radiation, of the layer of SU-8-resin through the mask, (b4) elimination of the mask and of the nonirradiated resin'

(b5) curing under annealing, between 70° C. and 120° C. for 1 minute, of the remaining resin.

9. The process as claimed in claim 1, wherein step (b) further comprises the following steps:

(b6) deposition of a positive-type resin, sensitive to UV radiation, on the sheet made of a fluoropolymer material comprising the at least two electrodes, (b7) irradiation, with said UV radiation, of the layer of sensitive resin through a mask made of a material which is transparent to said UV radiation, comprising an opening or a zone made of a material which is transparent to said UV radiation, this opening or zone having the shape of the at least two electrodes, (b8) removal of the mask and elimination of the irradiated resin, (b9) pyrolytic deposition of a layer of type N parylene ([2,2]-paracyclophane) or type C parylene (chloro-[2,2]-paracyclophane) in the zones where the resin has been eliminated, (b10) elimination of the remaining sensitive resin.

10. The process as claimed in claim 1, wherein step (b) further comprises the following steps:

(b11) electrografting of an electrophoretic polymer material onto the at least two electrodes, (b12) curing of the electrophoretic polymer material by heating.

11. The process as claimed in claim 1, wherein:

step f is a step of reaction of reactive functional groups of the biological molecule (A) with a zone of the microbeam functionalized with carboxylic acid functions functional groups, said process does not comprise a prefunctionalization step (d), and step (e) comprises the following steps:

(e5) deposition of a layer of positive-type resin, sensitive to UV radiation, on the sheet made of a fluoropolymer material, (e6) irradiation, by said UV radiation, of the layer of sensitive resin through a mask made of a material which is not transparent to said UV radiation, comprising an opening or a zone made of a material which is transparent to said UV radiation, this opening or this zone having the shape of the zone to be functionalized and being located in the part of the mask corresponding to the microbeam part to be formed and outside the zone of the microbeam in which the at least two electrodes is embedded or to be embedded, (e7) elimination of the irradiated resin and of the mask, (e8) formation of an acrylic acid polymer (PAA), in the zones where the resin has been eliminated, via diazonium salt technology, (e9) elimination of the remaining resin.

12. The process as claimed in claim 1, wherein:
step (f) is a step of reaction of reactive functional groups of the biological molecule (A) with functional groups of the microbeam other than carboxylic acid functional groups or alkene functional groups, or maleimide groups, or with activated ester groups,
said process comprises prefunctionalization step (d), and step (d) comprises the following steps:
(d1) deposition or grafting of a mask made of a material which is not transparent to VUV radiation, comprising an opening or a zone made of a material which is transparent to said VUV radiation, this opening or this zone having the shape of the zone of the sheet made of a fluoropolymer material to be functionalized, this opening or this zone being located in the part of the mask corresponding to the microbeam to be formed, and outside the zone of the microbeam in which the at least two electrodes is embedded or to be embedded,
(d2) irradiation, by said VUV radiation, under an inert gas of the sheet obtained in step (d1),
(d3) removal of the mask,
(d4) formation of a poly(acrylic acid) PAA polymer in the irradiated zones.

13. The process as claimed in claim 1, wherein:
step (f) is a step of reaction of reactive functional groups of the biological molecule (A) with functional groups of the microbeam other than carboxylic acid functional groups or alkene functional groups, or a maleimide group, or with an activated ester group, and
step (d) comprises the following steps:
(d5) deposition of a layer of positive-type resin, sensitive to UV radiation, on the sheet made of a fluoropolymer material,
(d6) irradiation, by said UV radiation, of the layer of sensitive resin through a mask made of a material which is not transparent to said UV radiation, comprising an opening or a zone made of a material which is transparent to said UV radiation, this opening or this zone having the shape of the zone to be functionalized and being located in the part of the mask corresponding to the microbeam part to be formed and outside the zone of the microbeam in which the at least two electrodes is embedded or to be embedded,
(d7) elimination of the irradiated resin and of the mask,
(d8) formation of an acrylic acid polymer (PAA), in the zones where the resin has been eliminated, via diazonium salt technology, and
(d9) elimination of the remaining resin.

14. The process as claimed in claim 12 or 13, wherein step (e) further comprises the following step:
(e10) modification, of the PAA formed in step (d4) or in step (d8), with an organic molecule, comprising, at its end not bonded to the PAA, $NH_2$, SH, $N_3$, OH or alkene functional groups, or maleimide groups, or activated ester groups.

15. The process as claimed in claim 1, wherein:
step (f) is a step of grafting of reactive functional groups of the biological molecule (A) with diazonium functional groups of the microbeam,
said process comprises a prefunctionalization step (d), and
step (d) comprises the following steps:
(d10) deposition of a layer of positive-type resin, sensitive to UV radiation, on the sheet made of a fluoropolymer material,
(d11) irradiation, by said UV radiation, of the layer of sensitive resin through a mask made of a material which is not transparent to said UV radiation, comprising an opening or a zone made of a material which is transparent to said UV radiation, this opening or this zone having the shape of the zone to be functionalized, and being located in the part of the mask corresponding to the microbeam but outside the zone of the microbeam in which the at least two electrodes are embedded or are to be embedded,
(d12) elimination of the irradiated resin,
(d13) removal of the mask,
(d14) grafting of a layer of poly(aminophenylene) polymer onto the zone where the resin has been eliminated, and
step (e) is a step (e11) of activation of the layer of poly(aminophenylene) polymer formed in step (e14) to give a layer of poly(diazonium phenylene).

16. The process as claimed in claim 1, wherein the method further comprises step (d) which further comprises the following steps:
(d15) deposition or grafting, onto the sheet made of a fluoropolymer material, of a mask, made of a material which is not transparent to said VUV radiation, comprising an opening or a zone made of a material which is transparent to VUV radiation, this opening or this zone having the desired shape of the zone to be functionalized, and being located in the zone of the mask corresponding to the microbeam to be formed but outside that in which the at least two electrodes are embedded or are to be embedded,
(d16) irradiation, by said VUV radiation, under an inert gas, of the sheet obtained in step (e15),
(d17) removal of the mask,
(d18) formation of a layer of an acrylic acid polymer (PAA) in the irradiated zones obtained in step (d16),
(d19) binding of $Cu^{2+}$ ions, by chelation, onto the PAA grafted in step (d18),
(d20) growth, in the zones where the $Cu^{2+}$ ions were bound, of a layer made of a metal chosen from copper, gold, platinum or silver, by reduction of the $Cu^{2+}$ ions when the layer to be formed must be made of copper, or in a bath of the desired metal, when the layer to be formed must be made of a metal other than copper.

17. The process as claimed in claim 1, wherein the process further comprises step (d) which further comprises the following steps:
(d21) deposition of a layer of positive-type resin, sensitive to UV radiation, on the sheet made of a fluoropolymer material,
(d22) irradiation, with said UV radiation, of the layer formed in step (d21), through a mask made of a material which is not transparent to said UV radiation, comprising an opening or a zone made of a material which is transparent to said UV radiation, this opening or this zone having the desired shape of the zone to be functionalized, and being located in the zone of the mask corresponding to the microbeam to be created but different than that in which the at least two electrodes is embedded or to be embedded,
(d23) elimination of the irradiated resin and removal of the mask,
(d24) grafting of a layer made of a PAA polymer, via diazonium salt technology, in the zones where the resin has been eliminated,
(d25) binding of $Cu^{2+}$ ions, by chelation, onto the PAA grafted in step (d24), in the zones where the resin has been eliminated, (d26) growth, in the zones where the $Cu^{2+}$ ions were bound, of a layer of metal chosen from copper, gold, platinum or silver, on the layer formed in step (d25), by reduction of the $Cu^{2+}$ ions, when the layer must be made of copper, or in a bath of the desired metal when the layer must be made of a metal other than copper, (d27) elimination of the remaining resin.

18. The process as claimed in claim 16 or 17, wherein step (f) is a step of reaction of a reactive functional group of the biological molecule (A) with a diazonium functional group of the microbeam and step (e) further comprises the following steps:

(e12) deposition of a positive-type resin, sensitive to UV radiation, on the sheet comprising a metalized zone obtained in step (d20) or on the sheet comprising a metalized zone obtained in step (d26), (e13) irradiation of the sheet obtained in step (e12), through a mask made of a material which is not transparent to said UV radiation, comprising an opening or a zone made of a material which is transparent to said UV radiation, this opening or this zone corresponding to the metalized zone of the sheet other than the at least two electrodes defined in step (a), (e14) elimination of the irradiated resin and of the mask, (e15) grafting of a layer of poly(aminophenylene) polymer onto the zone where the resin has been eliminated, (e16) elimination of the remaining resin, (e17) activation of the layer of poly(aminophenylene) to give a layer of poly(diazonium phenylene).

19. The process as claimed in claim 16 or 17, wherein the layer formed in step (d20) or in step (d27) is a layer of gold and in that functionalization step (e) comprises the following steps:

(e18) creation of a self-assembled layer of alkanethiol/Au on a metalized zone of the sheet, different than that or those where the at least two electrodes have been formed by means of step (a), (e19) bonding of the free part of the molecule corresponding to the alkanethiol of the self-assembled monolayer obtained in step (e18) with an organic molecule comprising $NH_2$, SH, $N_3$, OH or alkene free end functional groups, or a maleimide or activated ester, and wherein the biological molecule (A) is grafted with these functional groups to the reactive free end groups of the organic molecule grafted in step (e19).

20. The process as claimed in claim 16 or 17, wherein step (f) is a step of reaction of reactive functional groups of the biological molecule (A) with $NH_2$, SH, $N_3$, OH or alkene functional groups, or maleimide groups, or activated ester groups present on a zone of the microbeam, and step (e) comprises the following steps:

(e20) deposition of a positive-type resin, sensitive to UV radiation, on the sheet comprising a metalized zone obtained in step (d20) or on the sheet comprising a metalized zone obtained in step (d26), (e210 irradiation of the sheet obtained in step (e20), through a mask made of a material which is not transparent to said UV radiation, comprising an opening or a zone made of a material which is transparent to said UV radiation, this opening or this zone corresponding to the metalized zone of the sheet other than the at least two electrodes defined in step (a), (e22) elimination of the irradiated resin and of the mask, (e23) formation, via diazonium salt technology, in the zone irradiated in step (e21), of a polymer obtained from monomers comprising vinyl or acrylate functional groups, (e24) elimination of the remaining resin, (e25) modification of the polymer formed in step (e23) by reaction of the reactive groups of the polymer with the reactive groups of an organic molecule comprising $NH_2$, SH, $N_3$, OH or alkene free end functional groups, or maleimide, or activated ester, and wherein the biological molecule (A) is grafted onto the functional groups with free groups of the organic molecule preferred in step (e25).

21. The process as claimed in claim 1, wherein step (c) further comprises the following steps:

(c1) fabrication of a cutting mold which is hollow or is in the shape of the structure of the desired final sensor, (c2) compression of the mold fabricated in step (c1) on the sheet made of a fluoropolymer material, (c3) cutting of the desired structure around the mold by stamping with heating and/or ultrasonic acoustic excitation of the cutting mold, (c4) cutting of the desired shape in the sheet made of a fluoropolymer material, by means of an excimer material laser emitting in the VUV wavelength range, (c5) deposition of a mask or of a stencil comprising an opening silhouetting the desired final shape of the sensor on the sheet made of a fluoropolymer material, (c6) cutting, by deep reactive-ion etching (DRIE), of the outlines of the opening of the mask or of the stencil, (c7) fabrication of a cutting mold which is hollow or is in the shape of the structure of the desired final sensor made of a material or of an alloy having a hardness greater than the fluoropolymer material to be cut, (c8) compression of the mold fabricated in step (c7) on the sheet made of a fluoropolymer material, (c9) cutting of the desired structure around the mold by stamping at ambient temperature.

22. The process as claimed in claim 21, wherein step (c) further comprises a step (c10) of manual cutting under a microscope, of the shape of the final sensor.

23. A process for the fabrication of a biosensor, said biosensor comprising:

a microbeam, which is a mobile part of the biosensor, connected to a support, at least two electrodes, at least a part of each electrode being embedded in the microbeam, at least one biological molecule (A) grafted onto the microbeam in a location different from where said electrodes are embedded, a piezoelectric transducer for converting variations in the mechanical properties of the microbeam into an electrical signal, when the at least one biological molecule (A) is brought into contact with a biological molecule (B) to be detected and/or quantified, wherein the microbeam and its support are made of a fluoropolymer material and form an integral component, the process comprising the following steps:

(a) formation of at least two electrodes on a sheet made of a fluoropolymer material, (b) passivation of the at least two electrodes, (c) creation of a final desired shape of the biosensor in the sheet made of a fluoropolymer material, said desired shape being defined by the microbeam and its support both made of said fluoropolymer material and forming an integral component as well as the at least two electrodes at least a part of each electrode being embedded in the microbeam and, separation of the final desired shape from the sheet, (d) optionally, prefunctionalization of a zone of the microbeam, the zone being at a location different from where the at least two electrodes are embedded, (e) functionalization of either the zone prefunctionalized in step (d), when step (d) is carried out, or of a zone of the microbeam, this zone being different than the zone wherein the at least one electrode is embedded, (f) grafting of at least one biological molecule (A) onto the functionalized zone obtained in step (d), wherein step (a) further comprises the following steps:

(a35) deposition of a layer of positive-type resin, sensitive to UV radiation, on the surface of the sheet made of fluoropolymer material, (a36) irradiation, with said UV radiation, of the layer formed in step (a35), through a mask made of a material which is transparent to said UV radiation, comprising at least one opening or one zone made of a material which is transparent to said UV radiation, this opening or this zone having the desired shape of the at least two electrodes, (a37) elimination of the zones of irradiated resin and of the mask, (a38) deposition of gold in the zones in which the resin has been eliminated, by physical evaporation under vacuum, (a39) elimination of the remaining photosensitive resin.

24. A process for the fabrication of a biosensor, said biosensor comprising:
   a microbeam, which is a mobile part of the biosensor, connected to a support,
   at least two electrodes, at least a part of each electrode being embedded in the microbeam,
   at least one biological molecule (A) grafted onto the microbeam in a location different from where said electrodes are embedded,
   a piezoelectric transducer for converting variations in the mechanical properties of the microbeam into an electrical signal, when the at least one biological molecule (A) is brought into contact with a biological molecule (B) to be detected and/or quantified, wherein
   the microbeam and its support are made of a fluoropolymer material and form an integral component,
the process comprising the following steps:
(a) formation of at least two electrodes on a sheet made of a fluoropolymer material,
(b) passivation of the at least two electrodes,
(c) creation of a final desired shape of the biosensor in the sheet made of a fluoropolymer material, said desired shape being defined by the microbeam and its support both made of said fluoropolymer material and forming an integral component as well as the at least two electrodes at least a part of each electrode being embedded in the microbeam and, separation of the final desired shape from the sheet,
(d) optionally, prefunctionalization of a zone of the microbeam, the zone being at a location different from where the at least two electrodes are embedded,
(e) functionalization of either the zone prefunctionalized in step (d), when step (d) is carried out, or of a zone of the microbeam, this zone being different than the zone wherein the at least one electrode is embedded,
(f) grafting of at least one biological molecule (A) onto the functionalized zone obtained in step (d), wherein:
step (f) is a step of grafting of reactive functional groups of the biological molecule (A) with a zone of the microbeam functionalized with carboxylic acid functional groups (COOH),
said process does not comprise a prefunctionalization step (d), and
step (e) further comprises the following steps:
(e1) deposition or grafting of a mask made of a material which is not transparent to VUV radiation, comprising an opening or a zone made of a material which is transparent to said VUV radiation, this opening or this zone having the shape of the zone of the sheet made of a fluoropolymer material to be functionalized, this opening or this zone being located in the part of the mask corresponding to the microbeam to be formed, and outside the zone of the microbeam in which the at least two electrodes are embedded or to be embedded,
(e2) irradiation, by said VUV radiation, under an inert gas of the sheet obtained in step (e2)
(e3) removal of the mask,
(e4) formation of a poly(acrylic acid) (PAA) polymer, in the irradiated zones.

* * * * *